(12) United States Patent
Clemens (10) Patent No.: US 10,464,099 B2
(45) Date of Patent: Nov. 5, 2019

(54) DISPENSING PLUNGER, DISPENSING APPARATUS COMPRISING THE DISPENSING PLUNGER AND METHOD

(71) Applicant: SULZER MIXPAC AG, Haag (CH)

(72) Inventor: Victor Clemens, Bregenz (AT)

(73) Assignee: SULZER MIXPAC AG, Haag (CH)

( * ) Notice: Subject to any disclaimer, the term of this patent is extended or adjusted under 35 U.S.C. 154(b) by 22 days.

(21) Appl. No.: 15/030,483

(22) PCT Filed: Oct. 13, 2014

(86) PCT No.: PCT/EP2014/071913
§ 371 (c)(1),
(2) Date: Apr. 19, 2016

(87) PCT Pub. No.: WO2015/062855
PCT Pub. Date: May 7, 2015

(65) Prior Publication Data
US 2016/0243581 A1    Aug. 25, 2016

(30) Foreign Application Priority Data

Oct. 29, 2013   (EP) .................................... 13190744

(51) Int. Cl.
| | | |
|---|---|---|
| *B05C 17/005* | (2006.01) | |
| *B05C 17/01* | (2006.01) | |
| *A61C 5/62* | (2017.01) | |
| *A61C 5/64* | (2017.01) | |
| *A61C 5/66* | (2017.01) | |

(52) U.S. Cl.
CPC .......... *B05C 17/00583* (2013.01); *A61C 5/62* (2017.02); *A61C 5/64* (2017.02);
(Continued)

(58) Field of Classification Search
CPC ........ B05C 17/00583; B05C 17/00596; B05C 17/00553; B05C 17/0103;
(Continued)

(56) References Cited

U.S. PATENT DOCUMENTS 5,253,785 A * 10/1993 Haber ..................... A61M 5/19
222/135
5,593,066 A * 1/1997 Konuma ........... B05C 17/00506
222/105
(Continued)

FOREIGN PATENT DOCUMENTS

| EP | 1336575 A2 | 8/2003 |
|---|---|---|
| EP | 2314383 A1 | 4/2011 |

(Continued)

OTHER PUBLICATIONS

International Preliminary Report on Patentability and Written Opinion dated May 3, 2016 in PCT/EP2014/071913, filed Oct. 13, 2014.

*Primary Examiner* — Paul R Durand
*Assistant Examiner* — Robert K Nichols, II
(74) *Attorney, Agent, or Firm* — Global IP Counselors, LLP (57) ABSTRACT

A dispensing apparatus is suitable for the reception of a cartridge containing a dispensable medium. A dispensing plunger is configured to be arranged at or in the dispensing apparatus, the dispensing plunger having an end face which acts on the cartridge for a dispensing of the medium out of the cartridge. The dispensing plunger is configured such that the end face, during the dispensing of the medium, has at least a first dispensing cross-section and subsequently has at least a second dispensing cross-section.

18 Claims, 5 Drawing Sheets

(52) U.S. Cl.
CPC .......... *A61C 5/66* (2017.02); *B05C 17/00553* (2013.01); *B05C 17/00576* (2013.01); *B05C 17/00596* (2013.01); *B05C 17/0103* (2013.01)

(58) Field of Classification Search
CPC ....... B05C 17/00576; A61C 5/66; A61C 5/62; A61C 5/64; A61C 9/0026; A61M 5/31515; A61M 5/19; A61B 17/00491; B65D 81/325; B65D 83/0033; B65D 83/64; B65D 83/0072; B05B 11/0048
USPC .................................. 222/325, 386, 94, 135
See application file for complete search history.

(56) References Cited

U.S. PATENT DOCUMENTS

| | | |
|---|---|---|
| 6,454,138 B1 | 9/2002 | Greenhill et al. |
| 6,681,957 B1 | 1/2004 | Green |
| 2002/0098462 A1* | 7/2002 | Kaneko .................... A61C 5/66 433/89 |
| 2008/0011784 A1* | 1/2008 | Schneider ......... B05C 17/00513 222/333 |
| 2008/0195082 A1* | 8/2008 | Pauser ................. A61C 9/0026 604/518 |
| 2010/0108709 A1* | 5/2010 | Frey .................. B05C 17/00516 222/1 |
| 2013/0026182 A1 | 1/2013 | Habibi-Naini |
| 2015/0114986 A1* | 4/2015 | Ngu .................. B05C 17/00553 222/94 |
| 2015/0250463 A1* | 9/2015 | Jamiolkowski .. A61B 17/00491 604/500 |

FOREIGN PATENT DOCUMENTS

| | | |
|---|---|---|
| WO | 9947433 A1 | 9/1999 |
| WO | 2011131483 A1 | 10/2011 |

* cited by examiner

DISPENSING PLUNGER, DISPENSING APPARATUS COMPRISING THE DISPENSING PLUNGER AND METHOD

CROSS-REFERENCE APPLICATION

This application is a U.S. National Stage Application of International Application No. PCT/EP2014/071913, filed Oct. 13, 2014, which claims priority to European Application No. 13190744.6, filed Oct. 29, 2013, the contents of each of which is hereby incorporated herein by reference.

BACKGROUND

Field of Invention

The invention relates to a dispensing plunger, to a dispensing apparatus comprising the dispensing plunger, as well as to a method for dispensing a medium out of a collapsible cartridge.

Background Information

Cartridges are frequently used in an industrial setting, in the construction sector, for example in the construction of buildings and/or structures, as well as in the dental field, in order to store flowable substances and to dispense these as required for the respective application. Examples for such substances are caulking compounds, compounds for chemical dowels or chemical anchors, adhesives, pastes or impression compounds in the dental field. These cartridges are typically made of plastic and are produced in an injection molded process.

One difference between one component systems in which the material to be dispensed is only composed of one component and two-component or multi-component systems in which at least two different components are stored in separate chambers of the same cartridge or in separate cartridges, wherein the components are mixed on dispensing by a dynamic mixing apparatus or a static mixing apparatus. An example of this is a two-component adhesive which only hardens once the two components have been mixed.

SUMMARY

From WO 2011/131483 A1 a cartridge capable of standing is known having at least one reception chamber for a medium to be dispensed extending in the longitudinal direction, comprising a cartridge base and comprising a cartridge wall which bound the reception chamber, wherein the cartridge is produced by a thermo forming process or a blow molding process and is configured collapsible in a controllable manner.

However, under some circumstances this known prior art has the effect that a residual volume can remain in the cartridge at the end of the dispensing on a collapsing of the cartridge for a dispensing of the medium, since the dispensing plunger of the dispensing apparatus can possible not further compress the cartridge wall, amongst other things due to the formation of creases at a cartridge wall of the cartridge on collapsing.

For this reason, it is an object of the present invention to avoid the disadvantages of the known prior art, in particular to thus provide a dispensing plunger, a dispensing apparatus and a method for dispensing a dispensable medium out of a collapsible cartridge so that the remaining residual volume in the cartridge can be minimized.

These objects are satisfied by the dispensing plunger, a dispensing apparatus comprising the dispensing plunger, as well as by the corresponding method in accordance with the independent claims.

The dependent claims relate to particularly advantageous embodiments of the invention.

The invention relates to a dispensing plunger for a dispensing apparatus. The dispensing apparatus is suitable for the reception of a cartridge including a dispensable medium, wherein the cartridge is collapsible. The dispensing plunger can be arranged at and/or in the dispensing apparatus, wherein the dispensing plunger has an end face which can act on the cartridge for a dispensing of the medium out of the cartridge. The dispensing plunger is configured in such a way that the end face has at least a first dispensing cross-section during a dispensing of the medium and subsequently has at least a second dispensing cross-section. The first dispensing cross-section and the second dispensing cross-section in particular have a different size and/or shape.

The change of the cross-section of the dispensing plunger during the dispensing of the medium has the advantage that the remaining residual volume in the cartridge can be minimized, regardless of the design of the cartridge and/or of the dispensing apparatus that. This is achieved thereby by the cross-section of the end face being reduced, increased or changed in shape. Naturally, the size of the cross-section can remain constant during the change of the shape or, however, the change in shape can be combined with a reduction of the cross-section or an increase of the cross-section.

A dispensing cross-section of the dispensing plunger in the sense of the present application is understood as the cross-section of the end face which is moved in the dispensing direction during correct dispensing of the medium and which can thus acts on the cartridge. In this connection, the cross-section is determined substantially perpendicular to the dispensing direction.

Such a change in cross-section can, for example, take place through the use of two dispensing plungers which can be used following one another and which have different cross-sections. Moreover, it is plausible to use a dispensing plunger of modular design which can have a different cross-section in dependence on a position of the dispensing plunger at and/or in the dispensing apparatus. The modules of the dispensing plunger can be coupled and/or decoupled for this purpose, wherein the coupling and/or decoupling of the modules can take place mechanically or also electromagnetically, for example, by a switchable electro-magnet, wherein the coupling and/or decoupling can take place in a controlled or regulated manner. The modules of the dispensing plunger can be configured as couplable and/or decouplable plungers. The dispensing plunger of modular design can naturally also comprise non-coupled modules, in particular plungers, wherein a drive comprises at least two controllable and/or regulatable modular drives which are connected to the modules in an effective manner in such a way that the end face of the dispensing plunger has at least a first dispensing cross-section during a dispensing of the medium and subsequently has at least a second dispensing cross-section.

The collapsible cartridge can have a reception volume for the medium in the range of 10 ml to 1000 ml, preferably of 25 ml to 600 ml and particularly preferably of 50 ml to 300 ml.

Preferably the first dispensing cross-section is larger than the second dispensing cross-section on a correct movement of the dispensing plunger along an axial dispensing direction. This configuration has the advantage, in particular, that when using collapsible cartridges that the cartridge wall is indeed compressed laterally in the dispensing apparatus, however, the dispensing plunger having a smaller second dispensing cross-section can still be moved further in a central region for a substantial dispensing of the residual volume.

The dispensing plunger is preferably composed of at least two parts and comprises a first plunger and a second plunger. The dispensing plunger particularly preferably comprises precisely one first plunger and one second plunger.

A coupling apparatus for coupling and/or decoupling the first plunger and the second plunger is arranged preferably at and/or in the dispensing plunger. A coupling and/or decoupling is in particular reversible.

The at least two-part design of the dispensing plunger as a first plunger and as a second plunger which can be coupled and/or decoupled has the advantage that a mechanical dispensing plunger can be made available in a simple and reliable manner by which the change in cross-section can be achieved which can moreover be operated in a simple manner.

The first dispensing cross-section in particular comprises the cross-section of the end face of the first plunger and of the second plunger. Furthermore, the second dispensing cross-section in particular comprises the cross-section of the end face of the second plunger and not that of the first plunger.

The second plunger is preferably arranged in the first plunger. The first plunger and the second plunger are in particular arranged substantially centered with respect to one another.

The first plunger is preferably designed at least in a section thereof as a hollow cylindrical shape for the reception of the second plunger.

The first plunger preferably comprises at least a first recess and the second plunger comprises at least a second recess. The first recess is in particular a first opening. The first recess and the second recess are arranged with respect to one another in such a way that at least one pin of the coupling apparatus can be movably arranged in the first recess and in the second recess. The second plunger in particular has exactly one second recess which is configured circumferentially running in the circumferential direction of the second plunger.

This configuration has the advantage that coupling and/or a decoupling of the plunger is enabled in a simple and reliable manner by the movement of the pin of the coupling apparatus which coupling and/or decoupling is in particular reversible.

Preferably at least two first recesses, preferably at least three first recesses and particularly preferably at least four first recesses and possibly corresponding second recesses are provided. The first recesses and possibly the second recesses are in particular arranged substantially equidistantly with respect to one another in the circumferential direction of the first plunger.

This configuration has the advantage that improved coupling of the plungers is enabled with regard to a possibly present high load through the arrangement of a plurality of recesses and pins which are spaced apart substantially equidistantly with respect to one another in the circumferential direction of the first plunger, whereby a possible decoupling likewise moreover becomes more reliable, since a canting of the pins is substantially avoided.

The at least one pin is preferably configured tapering at the side facing the second recess and/or at the side facing away from the second recess. The tapering region of the pin is in particular configured as a truncated cone.

The at least one pin is preferably movably arranged and can be moved between a coupling position and a decoupling position. The at least one pin can in particular be moved in a direction substantially perpendicular to the axial dispensing direction.

The design of the pin with tapering ends is in particular advantageous on movement of the pin between the coupling position and the decoupling position substantially perpendicular to the axial dispensing direction. Through the movement of the dispensing plunger a force is in this case exerted on the tapering section of the pin through the movement of the dispensing plunger for a corresponding arrangement of the pin, whereby the pin is moved away from the second plunger and the decoupling of the plunger can thus be achieved reliably. This has the further advantage that no additional drive is required for the coupling and/or decoupling.

The second plunger preferably has an entrainment apparatus, in particular at the side facing the end face for entraining the first plunger following the decoupling on a movement opposite to the dispensing apparatus. The entrainment apparatus is in particular configured as at least one lateral projection and preferably as an entrainer flange.

This configuration has the advantage that the decoupled plunger can be simply retracted by the operator and can possibly be coupled to, for example, use a further cartridge in the dispensing apparatus.

The dispensing plunger preferably has a support apparatus at the side facing away from the end face. The support apparatus is in particular configured as a lateral projection and preferably as a flange. The support apparatus is suitable for the support of the dispensing plunger at a support cartridge of the dispensing apparatus in a position of cross-sectional change in particular in a decoupled position.

This configuration has the advantage that the first plunger can possibly be reliably maintained in the decoupled position and that the decoupling can be achieved reliably. Moreover, it can thereby be ensured that a force exerted onto the decoupling device is not so large and does not damage the device.

A further aspect of the present invention relates to a dispensing apparatus comprising a support cartridge for the reception of the collapsible cartridge. The dispensing apparatus further comprises a dispensing plunger as described in the foregoing.

The support cartridge preferably comprises one depression for the engagement for the at least one pin in the decoupled position. The depression is in particular configured tapering away from the dispensing plunger in a section thereof and preferably has a chamfer. The section of the recess tapering away is in particular configured at least in a region substantially complementary to the tapering end of the pin. The support cartridge in particular has precisely one depression which is configured running circumferentially in the circumferential direction of the support cartridge.

The design of the depression having a chamfer is in particular advantageous on movement of the pin between the coupling position and the decoupling position substantially perpendicular to the axial dispensing direction. Through the movement of the dispensing plunger opposite to the dispensing apparatus a force is in this case exerted on the tapering section of the pin for a corresponding arrangement of the pin, whereby the pin can be moved in the direction of the second plunger and the coupling of the plunger can thus be reliably achieved. This has the further advantage that no additional drive is required for the coupling.

An additional aspect of the present invention relates to a method for the dispensing of a dispensable medium from a collapsible cartridge by means of a dispensing apparatus. The dispensing apparatus is in particular configured as described in the foregoing.

The method in accordance with the invention comprises the step of providing the dispensing apparatus comprising a support cartridge for the reception of the cartridge. The dispensing apparatus further comprises a dispensing plunger, wherein an end face of the dispensing plunger can act on the collapsible cartridge for a dispensing of the medium out of the dispensing cartridge. The end face has at least a first dispensing cross-section during a dispensing of the medium and subsequently has at least a second dispensing cross-section, wherein the first dispensing cross-section and the second dispensing cross-section in particular have a different size.

Subsequently, the step of dispensing the medium out of the collapsible cartridge takes place by means of the dispensing apparatus through a movement of the dispensing plunger along an axial dispensing direction, wherein a cross-sectional change from the first dispensing cross-section to the second dispensing cross-section takes place at a position of cross-sectional changed.

BRIEF DESCRIPTION OF THE DRAWINGS

The invention will be explained in more detail hereinafter with reference to the drawings.

DETAILED DESCRIPTION OF THE EMBODIMENTS

Figure 1:
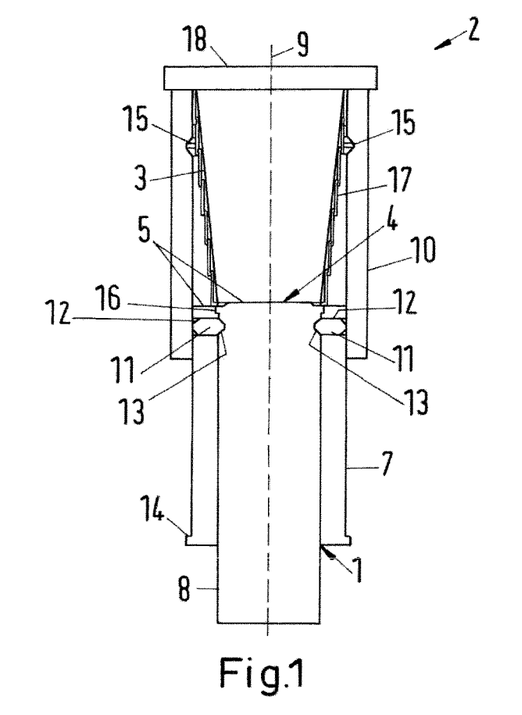
FIG. 1 is a schematic illustration of a dispensing apparatus in accordance with the invention.

In a schematic illustration FIG. 1 shows a dispensing apparatus 2 in accordance with the invention.

The dispensing apparatus 2 in accordance with FIG. 1 is present in a start position prior to the dispensing of a medium from a collapsible cartridge 3 which is arranged in the dispensing apparatus 2. The dispensing apparatus 2 comprises a support cartridge 10 for the reception of the cartridge 3. A sleeve 17 is moreover arranged in the support cartridge 10 which surrounds the cartridge in order to laterally support the cartridge 3 such that the cartridge 3 does not burst by means of the pressure exerted on the cartridge 3 for the dispensing. The sleeve 17 is configured to be telescopic in an axial direction 9 so that the collapsible cartridge 3 can be compressed for dispensing the medium.

A dispensing plunger 1 is partly arranged in the support cartridge 10, wherein the dispensing plunger 1 can act on the cartridge 3 by an end face 4 through a movement of the dispensing plunger 1 along the axial dispensing direction 9.

The dispensing plunger 1 is of two-part design and comprises a first plunger 7 and a second plunger 8. The second plunger 8 is arranged in the first plunger 7, wherein the first plunger 7 and the second plunger 8 are arranged substantially centered with respect to one another with reference to the longitudinal axes of the two plungers. The longitudinal axes of the two plungers are arranged substantially in parallel to the axial dispensing direction 9.

The first plunger 7 has a flange 14 for the support of the dispensing plunger 1 at the support cartridge 10 in a decoupled position of the first plunger 7 at the side facing away from the end face 4. The first plunger 7 further has a first recess which is configured as a first opening 12.

The second plunger 8 has an entrainment apparatus configured as an entrainer flange 16 for entraining the first plunger on a reverse movement of the dispensing plunger away from an outlet side 18 at the side facing the end face 4 so that following a decoupling of the first plunger 7 from the second plunger 8 a coupling of the plunger becomes possible.

Pins 11 are arranged in the first openings 12 and in the second recesses 13 for coupling and/or decoupling the plunger. Moreover, depressions 15 are arranged in the support cartridge 10. The pins 11 can be moved into the depressions 15 in the decoupled position. In this embodiment, the pins no longer engage in the second recesses 13 in such a way that decoupling of the plungers can take place.

The end face 4 has a first dispensing cross-section 5 which is formed by the end faces of the first plunger 7 and of the second plunger 8. The end face 4 in this connection acts on a movement of the dispensing plunger 1 with respect to the outlet side 18 towards the collapsible cartridge 3 such that the medium can be conveyed from the dispensing apparatus 2 through an outlet arranged in the outlet side 18. A static or dynamic mixing apparatus can be arranged at the outlet side 18 in accordance with the requirements, when, for example, the cartridge 3 includes at least two different components to be mixed as a medium. A conveying tube can also be arranged alternatively or additionally for conveying the medium to a position of application.

Figure 2:
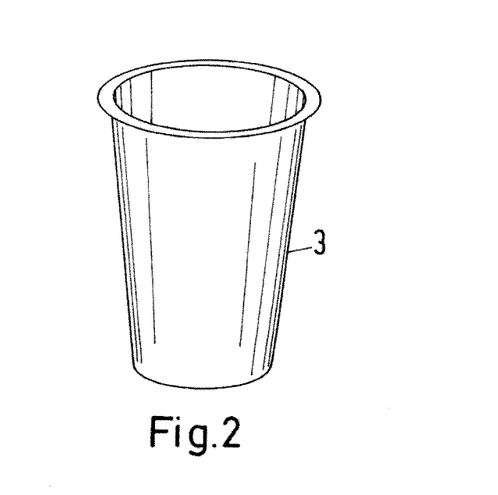
FIG. 2 is a perspective illustration of a cartridge for use in a dispensing apparatus in accordance with FIG. 1.

A collapsible cartridge 3 is shown in FIG. 2 in a perspective illustration, such as can be used in the dispensing apparatus in accordance with FIG. 1.

The same reference numerals relate to like features in all Figures.

Figure 3:
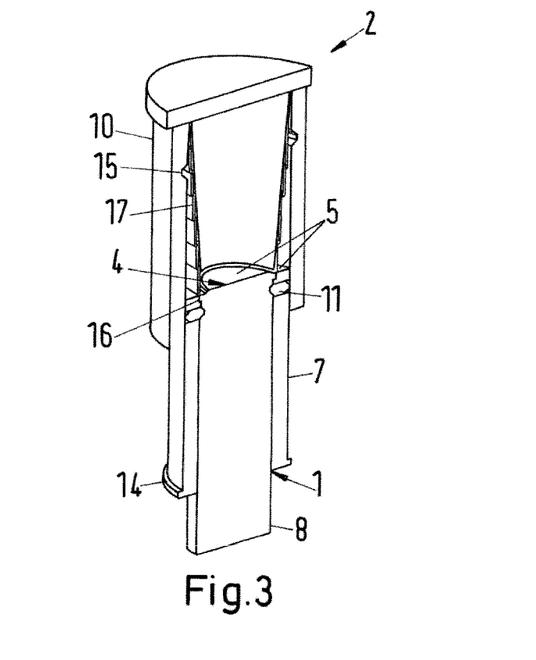
FIG. 3 is a perspective illustration of the dispensing apparatus in accordance with FIG. 1 in a first position.
Figure 4:
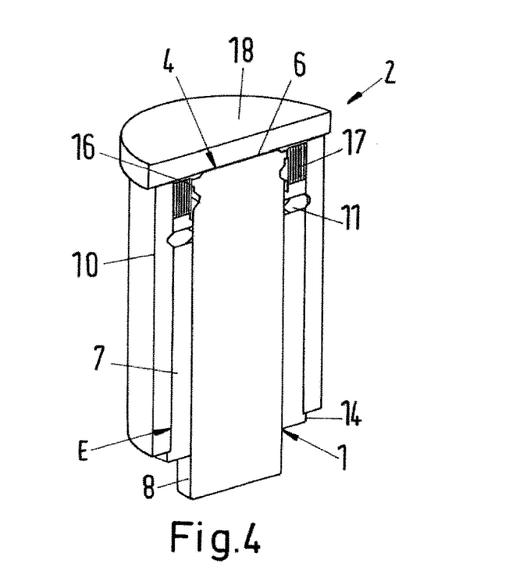
FIG. 4 is a perspective illustration of the dispensing apparatus in accordance with FIG. 1 in a second position.

The dispensing apparatus 2 in accordance with FIG. 1 is shown in a perspective illustration in two positions in the FIGS. 3 and 4. FIG. 3 shows the dispensing apparatus 2 in a first position with the end face 4 which has the first dispensing cross-section 5. The first plunger 7 and the second plunger 8 are coupled by the pins 11.

The dispensing plunger 1 is moved towards the outlet side 18 in FIG. 4. Hereby the first plunger 7 is moved with the second plunger 8 such that the first plunger has reached the decoupled position E in such a way that the flange 14 contacts the support cartridge 10 and thus the first plunger 7 is supported at the support cartridge 10. The pins 11 are moved into the depressions 15 through the force exerted in the axial dispensing direction 9 towards the outlet side 18 in the decoupled position E due to the ends thereof being configured as a truncated cone which pins engage in the second recesses 13 of the second plunger 8. A decoupling of the two plungers is hereby effected. Subsequently, the second plunger 8 can be moved further towards the outlet side 18. The dispensing plunger 1 has an end face 4 having the second dispensing cross-section 6 following the decoupling.

The dispensing plunger 1 is thus configured as a two-stage dispensing plunger 1 with respect to the end face 4.

During the movement of the dispensing plunger 1 towards the outlet side 18 a telescopic movement of the sleeves 17 is effected in such a way that the collapsible cartridge 3 is correspondingly laterally supported and that a dispensing of the medium is enabled at the same time.

Naturally, it is also possible to use the collapsible cartridge 3 without the sleeve 17 in the dispensing apparatus 2.

The second plunger 8 has the entrainer flange 16. On the reverse movement of the second plunger from the position such as is shown in FIG. 4 to the position in accordance with FIG. 3 an entrainment of the first plunger 7 by the second plunger 8 takes place. Hereby a force is exerted on the pin 11 by means of the first plunger 7 in such a way that the pin is moved out of the depression 15 and the plungers are again coupled.

On this movement back to the position in accordance with FIG. 3, the sleeve 17 is furthermore moved apart again.

Figure 5:
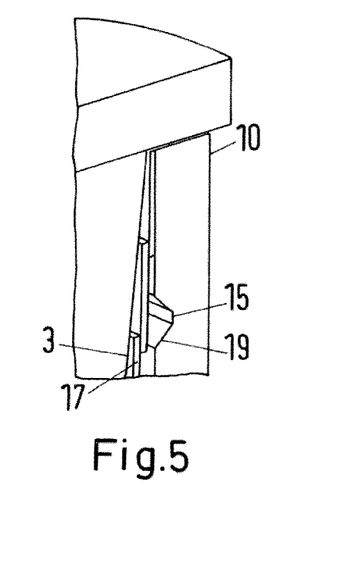
FIG. 5 is a perspective illustration of the section of a dispensing apparatus in accordance with FIG. 3.
Figure 6:
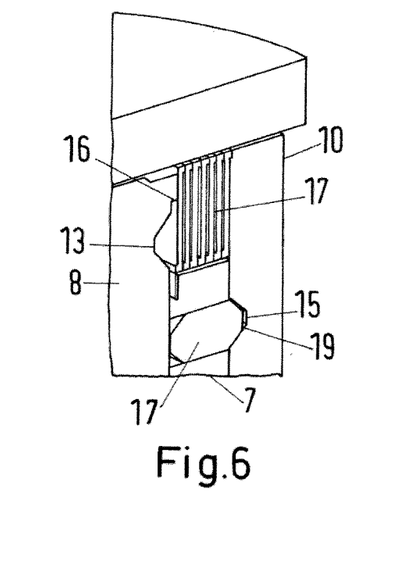
FIG. 6 is a perspective illustration of a section of the dispensing apparatus in accordance with FIG. 4.

Sections of the FIGS. 3 and 4 are illustrated in the FIGS. 5 and 6 in an enlarged manner. In FIG. 5 the design of the depression 15 having a chamfer 19 is shown to better enable the coupling and decoupling of the plunger as described above. The plungers are not visible in this example and are present in the coupled state.

In FIG. 6 the coupled state of the plunger is visible. The pin 11 is moved from the second recess 13 into the depression 15 having the chamfer 19. The second recess 13 is likewise configured as tapering away from the support cartridge 10. The pin 11 has a frustoconical shape at both ends.

Figure 7:
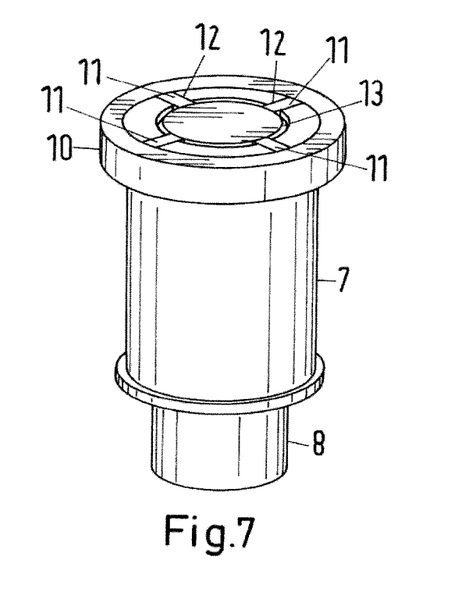
FIG. 7 is a perspective illustration of a part of the dispensing apparatus in accordance with FIG. 3 with a visible coupling apparatus.

A part of the dispensing apparatus in accordance with FIG. 3 with a visible coupling apparatus is shown in FIG. 7 in a perspective illustration, wherein the dispensing apparatus 2 in accordance with FIG. 3 is cut perpendicular to the axial dispensing direction 9 through the coupling apparatus and in this example the part facing away from the outlet side is shown. The coupling apparatus in this connection comprises the pins 11 which are arranged in first openings 12. Moreover, precisely one second recess 13 is circumferentially provided which is configured in the circumferential direction of the second plunger 8.

The first plunger 7 has four first openings 12 in which the pins 11 are arranged. The first openings 12 are equidistantly spaced apart with respect to one another in the circumferential direction of the first plunger 7.

The second plunger has precisely one circumferential second recess 13 in which the pins 11 can be moved. The arrangement of precisely one circumferential second recess 13 has the advantage that the first plunger 7 and the second plunger 8 can be rotated relative to one another without the functionality of the coupling and decoupling being influenced.

Figure 8:
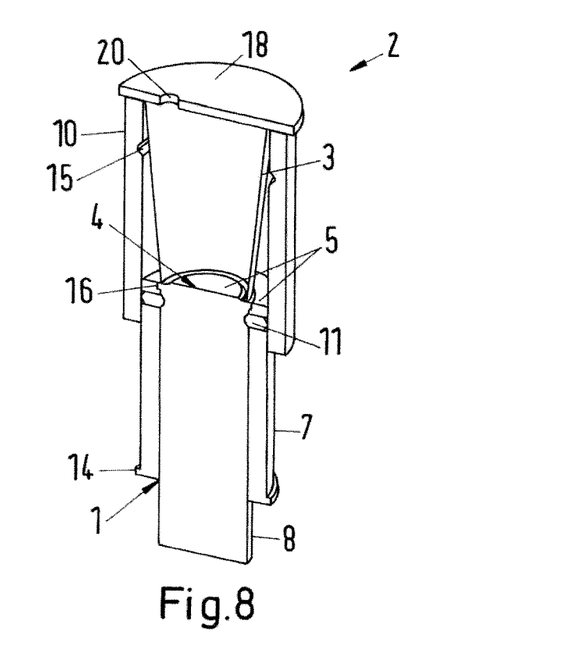
FIG. 8 is a perspective illustration of an alternative dispensing apparatus in accordance with the invention in a start position.

An alternative dispensing apparatus 2 in accordance with the invention is shown in a start position in a perspective illustration in FIG. 8. The dispensing apparatus 2 is configured substantially like the dispensing apparatus in accordance with FIG. 3.

In contrast to FIG. 3 an outlet 20 is shown in the outlet side 18 in the dispensing apparatus 2 in accordance with FIG. 8. Moreover, no sleeve is provided in the support cartridge 10 in contrast to FIG. 3.

Figure 9:
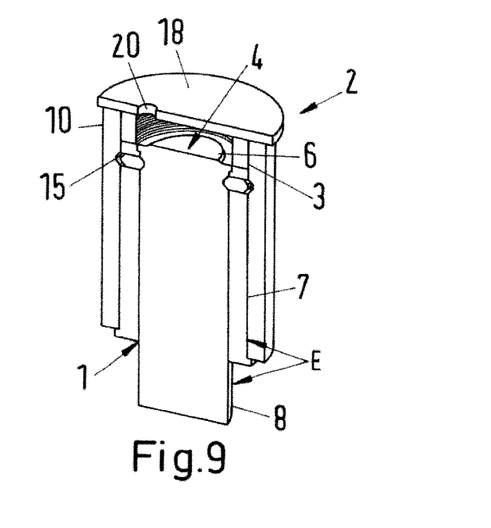
FIG. 9 is a perspective illustration of the dispensing apparatus in accordance with FIG. 8 in a decoupled position.

The dispensing apparatus 2 in accordance with FIG. 8 is illustrated in the decoupled position in FIG. 9. The first plunger 7 and the second plunger 8 of the dispensing plunger 1 are in this connection present in the decoupled position E. The cartridge 3 was collapsed for the dispensing of the medium.

Figure 10:
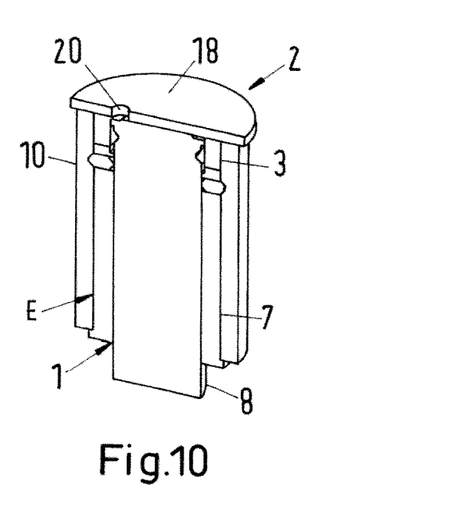
FIG. 10 is a perspective illustration of the dispensing apparatus in accordance with FIG. 8 in a final position.

The dispensing apparatus 2 in accordance with FIG. 8 is illustrated in an end position in FIG. 10. The first piston 7 in this connection remains in the decoupled position E, wherein the second piston 8 is moved further toward the outlet side 18.

Figure 11:
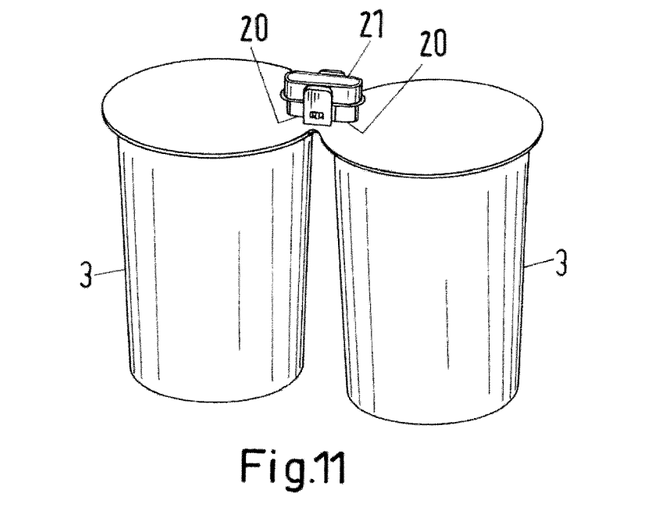
FIG. 11 is a perspective illustration of two cartridges for a dispensing apparatus.
Figure 12:
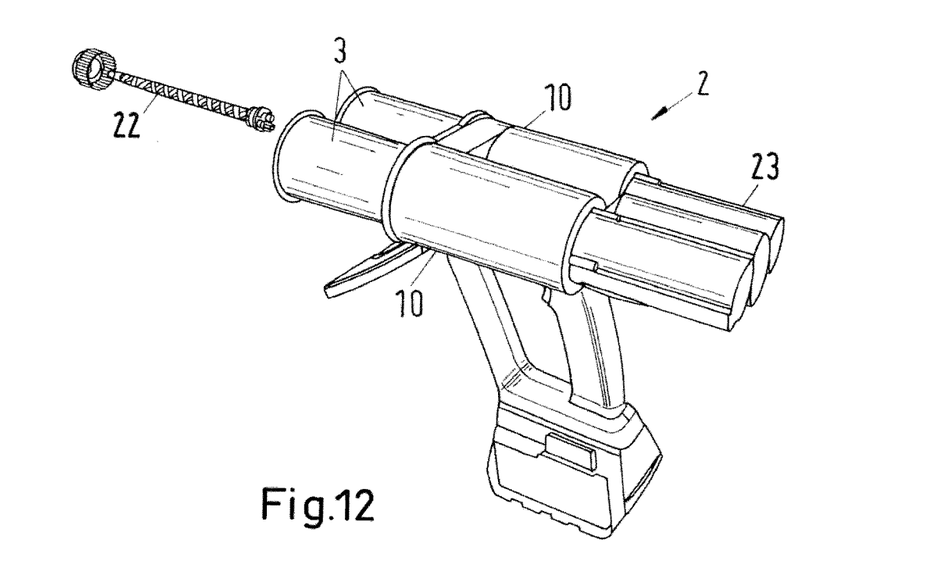
FIG. 12 is a perspective illustration of a dispensing apparatus for the two cartridges in accordance with FIG. 11.

Two cartridges 3 for the reception in a dispensing apparatus in accordance with FIG. 12 are illustrated in a perspective illustration in FIG. 11.

The cartridges 3 have outlets 20 as well as a fastening apparatus 21, for example, for a static mixer. Naturally also different application apparatuses such as e.g. cannulas can be arranged at the fastening apparatus 21.

Typically the two cartridges include different adhesive components which can be mixed by a static mixer arranged downstream of the outlets 20 at the fastening apparatus 21.

A dispensing apparatus 2 in accordance with the invention is shown in a perspective illustration in FIG. 12.

The dispensing apparatus 2 has a support cartridge 10 configured for the reception of the two cartridges 3. Moreover, the dispensing apparatus 2 comprises a static mixer 22 which can be fastened to the fastening apparatus 21 illustrated in the FIG. 11.

The dispensing apparatus 2 further comprises a drive 23 comprising an electric motor for actuating the dispensing plunger not visible in this example. The dispensing apparatus 2 comprises two dispensing plungers for the substantially simultaneous dispensing out of the two cartridges 3.

The dispensing plungers in this connection can be configured as illustrated in FIG. 8.

Alternatively, the dispensing plunger can be configured as non-coupled dispensing plungers, wherein the drive 23 for each cartridge can have two plunger drives (not shown) which are effectively coupled to the plungers in such a way that the end face of the dispensing plunger has at least a first dispensing cross-section during the dispensing of the medium and subsequently has at least a second dispensing cross-section.

What is claimed is:

1. A dispensing plunger for a dispensing apparatus for the reception of a collapsible cartridge containing a dispensable medium, the dispensing plunger being configured to be arranged at or in the dispensing apparatus, the dispensing plunger comprising:
an end face configured to act on the collapsible cartridge to dispense the dispensable medium out of the collapsible cartridge, the dispensing plunger being configured such that the end face, while dispensing the dispensable medium, has at least a first dispensing area acting on the collapsible cartridge and subsequently has at least a second dispensing area acting on the collapsible cartridge, the first dispensing area being larger than the second dispensing area on intended movement of the dispensing plunger along an axial dispensing direction;
a first plunger and a second plunger, which configure the dispensing plunger in at least two parts, and
the first plunger, in at least in a section thereof, includes a hollow cylindrical shape configured to receive the second plunger, the first plunger comprising at least a first recess, with the first recess being a first opening, and the second plunger comprising at least a second recess; and a pin movably arranged in the first recess and in the second recess to enable a change between the first dispensing area and the second dispensing area, the first recess and the second recess being arranged with respect to one another so that the pin is capable of being movably arranged in the first recess and in the second recess.

2. The dispensing plunger in accordance with claim 1, wherein the pin is at least part of a coupling apparatus configured to couple or decouple the first plunger and the second plunger, the coupling apparatus being arranged at or in the dispensing plunger.

3. The dispensing plunger in accordance with claim 2, wherein the coupling apparatus is configured for reversible coupling or decoupling.

4. The dispensing plunger in accordance with claim 1, wherein the second plunger is arranged in the first plunger.

5. The dispensing plunger in accordance with claim 4, wherein the first plunger and the second plunger are arranged centered with respect to one another.

6. The dispensing plunger in accordance with claim 1, wherein the first recess is one of at least two first recesses, and the second recess is one of at least two second recesses, and the at least two first recesses are disposed spaced apart with respect to one another equidistantly in the circumferential direction of the first plunger.

7. The dispensing plunger in accordance with claim 1, wherein the pin tapers at a side facing the second recess or a side facing away from the second recess.

8. The dispensing plunger in accordance with claim 7, wherein the pin is a truncated cone.

9. The dispensing plunger in accordance with claim 1, wherein the pin is movably arranged so as to be movable between a coupling position and a decoupling position.

10. The dispensing plunger in accordance with claim 9, wherein the pin is capable of being moved in a direction perpendicular to the axial dispensing direction.

11. The dispensing plunger in accordance with claim 1, further comprising a support apparatus at a side distal from the end face, and configured to support the dispensing plunger at a support cartridge of the dispensing apparatus in a position of area change, the support apparatus being a flange.

12. The dispensing plunger in accordance with claim 1, wherein the first dispensing area and the second dispensing area have a different shape.

13. The dispensing plunger in accordance with claim 1, wherein, a combination of the first plunger and the second plunger has the first dispensing area and the second plunger has a second dispensing area, and the first dispensing area being larger than the second dispensing area is a result of the second plunger decoupling from the first plunger during dispensing.

14. A dispensing plunger for a dispensing apparatus for the reception of a collapsible cartridge containing a dispensable medium, the dispensing plunger being configured to be arranged at or in the dispensing apparatus, the dispensing plunger comprising:

an end face configured to act on the collapsible cartridge to dispense the dispensable medium out of the collapsible cartridge, the dispensing plunger being configured such that the end face, while dispensing the dispensable medium, has at least a first dispensing area acting on the collapsible cartridge and subsequently has at least a second dispensing area acting on the collapsible cartridge, the first dispensing area being larger than the second dispensing area on intended movement of the dispensing plunger along an axial dispensing direction;

a first plunger and a second plunger, which configure the dispensing plunger in at least two parts; and a pin movably arranged in a first recess and in a second recess to enable a change between the first dispending area and the second dispensing area, the second plunger comprising an entrainment apparatus configured to entrain the first plunger following decoupling on movement opposite to a dispensing direction, the entrainment apparatus comprising at least one lateral projection and an entrainer flange at a side adjacent the end face.

15. A dispensing apparatus comprising:

a support cartridge configured to receive a collapsible cartridge;

a dispensing plunger, the dispensing plunger being arranged at or in the dispensing apparatus and having an end face configured to act on the collapsible cartridge for dispensing a medium out of the collapsible cartridge, the dispensing plunger being configured such that the end face, while dispensing the medium, has at least a first dispensing area acting on the collapsible cartridge and subsequently at least a second dispensing area acting on the collapsible cartridge, the first dispensing area being larger than the second dispensing area on intended movement of the dispensing plunger along an axial dispensing direction; and a pin movably arranged in a first recess and in a second recess to enable a change between the first dispensing area and the second dispensing area, the support cartridge includes a depression configured to engage the pin in a decoupling position.

16. The dispensing apparatus in accordance with claim 7, wherein the depression tapers away from the dispensing plunger at least in a section thereof.

17. The dispensing apparatus in accordance with claim 7, wherein the depression has a chamfer.

18. A method for dispensing a dispensable medium from a collapsible cartridge, the method comprising:

providing a dispensing apparatus comprising a support cartridge for the reception of the collapsible cartridge and a dispensing plunger, the dispensing plunger including an end face for acting on the collapsible cartridge for dispensing of the dispensable medium out of the collapsible cartridge, the end face of the dispensing plunger, during the dispensing of the dispensable medium, has at least a first dispensing area acting on the collapsible cartridge and subsequently has at least a second dispensing area acting on the collapsible cartridge;

dispensing of the dispensable medium out of the collapsible cartridge by the dispensing apparatus through movement of the dispensing plunger along an axial dispensing direction, during the dispensing moving a pin from a first recess to a second recess to change from the first dispensing area to the second dispensing area at a position of area change, the first dispensing area being larger than the second dispensing area on the movement of the dispensing plunger along the axial dispensing direction.

* * * * *